United States Patent [19]
Stanley

[11] Patent Number: 5,912,145
[45] Date of Patent: Jun. 15, 1999

[54] NUCLEIC ACID ANALOGUE ASSAY PROCEDURES AND KITS

[75] Inventor: John Christopher Stanley, Cambridgeshire, United Kingdom

[73] Assignee: PNA Diagnostics A/S, Copenhageno, Denmark

[21] Appl. No.: 08/549,786

[22] PCT Filed: May 31, 1994

[86] PCT No.: PCT/GB94/01174

§ 371 Date: Mar. 1, 1996

§ 102(e) Date: Mar. 1, 1996

[87] PCT Pub. No.: WO94/28171

PCT Pub. Date: Dec. 8, 1994

[30] Foreign Application Priority Data

Jun. 2, 1993 [GB] United Kingdom .................. 9311386

[51] Int. Cl.⁶ .............................. C12Q 1/68; C12P 19/34; C07H 21/02
[52] U.S. Cl. ............................ 435/91.1; 435/6; 435/91.2; 536/23.1; 536/24.3; 536/24.33
[58] Field of Search ............................ 435/6, 91.1, 91.2; 536/23.1, 24.3, 24.33

[56] References Cited

FOREIGN PATENT DOCUMENTS

WO 92/20703  11/1992  WIPO .............................. C07K 5/00

OTHER PUBLICATIONS

Gilliland et al. "Analysis of cytokine mRNA and DNA: Detection and quantitation by competitive polymerase chain reaction" Proc. Natl. Acad. Sci. USA, vol. 87, pp. 2725–2729 Apr. 1990.

*Primary Examiner*—Ardin H. Marschel
*Assistant Examiner*—Jezia Riley
*Attorney, Agent, or Firm*—Nikaido Marmelstein Murray & Oram, LLP

[57] ABSTRACT

An assay procedure to quantify the amount of starting template in a nucleic acid amplification procedure such as PCR involves trying the amplification in the presence of varying amounts of a nucleic acid analogue which in sufficient quantity will inhibit said amplification procedure by selective interaction with a nucleic acid species present, e.g. a PNA as described in WO-02/20703. The amount of template is given by the amount of nucleic acid analogue critical to cause failure of said amplification procedure.

14 Claims, No Drawings

NUCLEIC ACID ANALOGUE ASSAY PROCEDURES AND KITS

The present invention relates to assay procedures involving nucleic acid analogues by which quantitative or semi-quantitative determinations of such analogues or nucleic acid sequences to which they hybridise can be made.

Nucleic acid amplification techniques are now in widespread use. These include the "PCR" (polymerase chain reaction) procedure described in EP-A-0200362 and EP-A-0201184, which is the technique in most widespread use, but also the "LCR" (ligase chain reaction) described in EP-A-0320308, the so-called "NASBA" or "3SR" technique which is described in "Proc. Natl. Acad. Sci. USA" Vol. 87 pp 1874–1878 March 1990 and "Nature" Vol. 350, No. 6313. pp 91–92 Mar. 7, 1991 and the "SDA" method described in "Nucleic Acid Research", Vol. 20 pp 1691–1696.

A number of strategies now exist to obtain quantitative information from amplification systems such as the polymerase chain reaction. In the simplest procedure the amount of amplified DNA produced by the test sample is compared directly with a set of standard reactions prepared with known amounts of the same DNA. A linear relationship has been shown to exist between the amount of DNA present in the sample and the amount of amplification product eventually formed in the PCR assay. However, the exponential nature of the PCR process means that minor differences in amplification efficiency between the sample tube and the separate tubes containing the known amounts of DNA will lead to large and unpredictable differences in the final product yield (Gilliland et al (1990) "Proc. Natl Acad Sci. USA" 87, 2725–2729). Such direct comparisons between the amount of PCR product from the sample and standards tubes are therefore fundamentally flawed. A number of alternative procedures have been proposed to overcome this problem. These include the use of limiting dilution of the sample (Thang et al (1991) "AIDS", 5,678–681) or the co-amplification of internal or external standards (Kellog et al (1990) "Anal. Biochem," 189, 202–208). The limiting dilution method is a very simple strategy that employs a Poisson distribution analysis of positive reactions to calculate the amount of the target sequence in the sample. The limiting dilution method has a fundamental limitation because the linear relationship that exists between the initial amount of template DNA in the sample and the amount of amplification product obtained is only maintained for amounts of starting DNA within a limited range. Hence the method is very imprecise when samples containing highly variable amounts of target DNA are examined. The alternative methods of co-amplification can provide a more reliable approach, in that they rely on the measurement of the ratio of target DNA and a co-amplified standard within the same tube. However, they still suffer from a number of difficulties. The co-amplification of internal standards, such as ubiquitously expressed genes that are also present in the sample DNA is limited in its usefulness by the difference in amplification efficiency that exists between target and reference sequences. This will affect the relative amounts of the products obtained in an uncontrollable manner. The alternative method of co-amplification of an external template possessing a similar length and the same primer recognition sequences as the target DNA is the most successful strategy so far for a quantitative PCR assay (Gilliland et al "Proc. Natl. Acad. Sci. USA" 87, 2725–2729) but it still has three major disadvantages. The first problem is that the product from the target DNA and the co-amplified reference standard must be separated, usually by gel electrophoresis, and the separated products must be quantified to determine the ratio of the products. Usually, 4 reactions or more are carried out at different dilutions of the external competitor template and the products from all these reactions must be scanned to provide a standard curve. The external competitive PCR approach is therefore restricted to measurement methods that are capable of separating different PCR fragments and this introduces further complexity and cost to the procedure. The second factor that restricts the usefulness of the external competitive PCR approach is that it cannot be used if the PCR products are to be detected directly without a prior separation e.g. in a commonly used procedure biotin labelled PCR products are captured by hybridising to a capture probe immobilised to a microwell surface and subsequently detected by an avidin enzyme conjugate probe, leading to color generation in the well. Distinguishing between control and test samples in this type of assay requires the use of additional wells and different capture probes. The third disadvantage of the external competitive PCR approach is that the external standard must be designed carefully to have exactly the same amplification characteristics as the target DNA from the sample. This is not easy to achieve and it requires considerable skill and expense to construct such an external standard and each assay must have a new external standard which greatly increases the cost of assay development.

WO-A-93/25706 (published after the priority date of the present application) discloses that certain nucleic acid analogues capable of hybridising with high affinity to nucleic acids can be used to inhibit nucleic acid amplification procedures such as PCR The preferred nucleic acid analogues are described in WO-A-92/20703.

It has now been appreciated that the dependence of the successful inhibition of such nucleic acid amplification procedures on the amount of nucleic acid analogue present provides a means for deriving information regarding the amount of a nucleic acid which is present in a sample or about the amount of a nucleic acid analogue which is present.

Accordingly, the present invention provides an assay procedure comprising attempting to perform a nucleic acid amplification procedure in the presence of a nucleic acid analogue which in sufficient quantity will inhibit said amplification procedure by selective interaction with a nucleic acid species present, wherein the amount of said nucleic acid or the amount of said nucleic acid analogue but not both is known or later otherwise determined, determining the success, failure, or degree of success of said amplification procedure and thereby deriving information regarding the amount of said nucleic acid species or nucleic acid analogue present.

In most cases it is envisaged that it will be said nucleic acid species which is present in unknown quantity and this is preferably a template for said amplification.

The procedure preferably further comprises repeating said attempted assay procedure one or more times using one or more different amounts of said nucleic acid analogue or one or more dilutions of the sample so as to derive information regarding the relative amounts thereof needed to be present to inhibit said amplification procedure.

Preferably, a calibration curve is established by carrying out the same amplification procedure using a series of known relative amounts of the nucleic acid species and the nucleic acid analogue.

Thus using known amounts of said nucleic acid one may establish a calibration curve of amplification product quantity at a particular nucleic acid template concentration against nucleic acid analogue concentration. One may then carry out the assay procedure on a sample containing an unknown amount of the nucleic acid, preferably simultaneously conducting a number of assay runs at different dilutions of the nucleic acid analogue to identify the dilution between which the amplification procedure moves from success to failure. This will produce a semi-quantitative estimate of the amount of nucleic acid initially present, as the quantity of nucleic acid analogue required for inhibition of the amplification will be proportional to the quantity of nucleic acid template present. Thus if one finds that a calibration curve based on xng of plasmid moves from successful amplification to failure at a y μM concentration of nucleic acid analogue, a sample requiring a 2y μM concentration of nucleic acid analogue for inhibition will contain approximately 2xng of template.

There are a number of important advantages provided by this new procedure which we refer to as quantitation by inhibition (QI). Firstly, the QI process is not a ratio approach and so it is not necessary to seek an internal standard for amplification, or to laboriously construct an external standard. In a QI PCR process, for example, the nucleic acid analogue can be directed against the primers and this is very simple to achieve since the sequences are already known. The QI process does not produce two products which must be separated and quantitated as must be done in the external standard approach. Hence, the QI process is well suited to the move favored methods of product detection such as hybridisation in a microplate well. The QI process does not require any dilution of the sample and no complex mathematical treatment of the results is required. The QI process is therefore far superior to the limiting dilution method. The QI process is largely unaffected by variations in amplification efficiencies in individual tubes since the results are scored by comparison to a threshold level alone.

The QI process is well suited to a semi-quantitative measurement. The dynamic range can be very large, or very small depending on the concentration range of nucleic acid analogue chosen. The QI process can employ a single concentration of inhibitor to give a simple YES/NO answer, or many concentrations in multiple wells to provide a near quantitative result. The imprecision of the QI process, in terms of misclassification of sample DNA concentration, is a function of the variation in the product amplification process at the threshold point only.

The nucleic acid analogue is preferably capable of hybridising to a nucleic acid of complementary sequence to form a hybrid which is more stable against denaturation by heat than a hybrid between the conventional deoxyribonucleotide corresponding in sequence to said analogue and said nucleic acid.

Preferably, said nucleic acid analogue is a peptide nucleic acid in which said backbone is a polyamide backbone, each said ligand being bonded directly or indirectly to an aza nitrogen atom in said backbone, and said ligand bearing nitrogen atoms mainly being separated from one another in said backbone by from 4 to 8 intervening atoms.

Preferably also, the nucleic acid analogue is capable of hybridising to a double stranded nucleic acid in which one strand has a sequence complementary to said analogue, in such a way as to displace the other strand from said one strand.

Preferably, the nucleic acid analogue has the general formula 1:

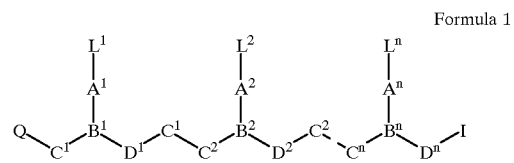

Formula 1 wherein:

n is at least 2, each of $L^1$–$L^n$ is independently selected from the group consisting of hydrogen, hydroxy, ($C_1$–$C_4$) alkanoyl, naturally occurring nucleobases, non-naturally occurring nucleobases, aromatic moieties, DNA intercalators, nucleobase-binding groups, heterocyclic moieties, and reporter ligands, but normally at least one L will be a nucleobase binding group such as a naturally occurring nucleobase and preferably at least 90% of the groups L will be such nucleobase binding groups;

each of $C^1$–$C^n$ is $(CR^6R^7)_y$, where $R^6$ is hydrogen and $R^7$ is selected from the group consisting of the side chains of naturally occurring alpha amino acids, or $R^6$ and $R^7$ are independently selected from the group consisting of hydrogen, ($C_2$–$C_6$) alkyl, aryl, aralkyl, heteroaryl, hydroxy, ($C_1$–$C_6$) alkoxy, ($C_1$–$C_6$) alkylthio, $NR^3R^4$ and $SR^5$, where $R^3$ and $R^4$ are as defined below, and $R^5$ is hydrogen, ($C_1$–$C_6$) alkyl, hydroxy, alkoxy, or alkylthio-substituted ($C_1$ to $C_6$) alkyl or $R^6$ and $R^7$ taken together complete an alicyclic or heterocyclic system;

each of $D^1$–$D^N$ is $(CR^6R^7)_z$ where $R^6$ and $R^7$ are as defined above;

each of y and z is zero or an integer from 1 to 10, the sum y+z being from 2 to 10 (preferably being more than 2, and most preferably each of y and z being 1 or 2;

each of $G^1$–$G^{n-1}$ is —$NR^3CO$—, —$NR^3CS$—, —$NR^3SO$— or —$NR^3SO_2$—, in either orientation, where $R^3$ is as defined below;

each of $A^1$–$A^n$ and $B^1$–$B^n$ are selected such that:

(a) A is a group of formula (IIa), (IIb), (IIc) or (IId), and B is N or $R^3N^+$; or (b) A is a group of formula (IId) and B is CH;

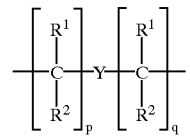

Formula IIa

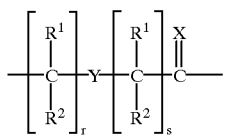

Formula IIb

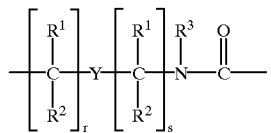

Formula IIc

-continued

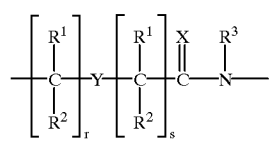

Formula IId wherein:
X is O, S, Se, NR³, CH₂ or C(CH₃)₂;
Y is a single bond, O, S or NR⁴;

each of p and q is zero or an integer from 1 to 5, the sum p+q being not more than 10;

each of r and s is zero or an integer from 1 to 5, the sum r+s being not more than 10;

each $R^1$ and $R^2$ is independently selected from the group consisting of hydrogen, ($C_1$–$C_4$) alkyl which may be hydroxy- or alkoxy- or alkylthio-substituted, hydroxy, alkoxy, alkylthio, amino and halogen; and each $R^3$ and $R^4$ is independently selected from the group consisting of hydrogen, ($c_1$–$C_4$) alkyl, hydroxy- or alkoxy- or alkylthio-substituted ($C_1$–$C_4$) alkyl, hydroxy, alkoxy, alkylthio and amino;

Q is —CO₂H, —CONR'R", —SO₃H or —SO₂NR'R" or an activated derivative of —CO₂H or —SO₃H; and I is —NR'R", where R' and R" are independently selected from the group consisting of hydrogen, alkyl, amino protecting groups, reporter ligands, intercalators, chelators, peptides, proteins, carbohydrates, lipids, steroids, nucleosides, nucleotides, nucleotide diphosphates, nucleotide triphosphates, oligonucleotides, including both oligoribonucleotides and oligodeoxyribonucleotides, oligonucleosides and soluble and non-soluble polymers.

More preferably, said nucleic acid analogue comprises a compound of the general formula III, IV or V:

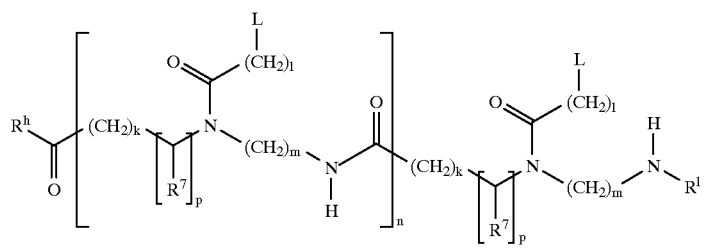

Formula III

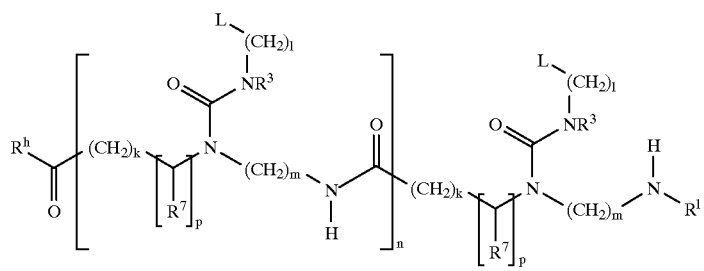

Formula IV

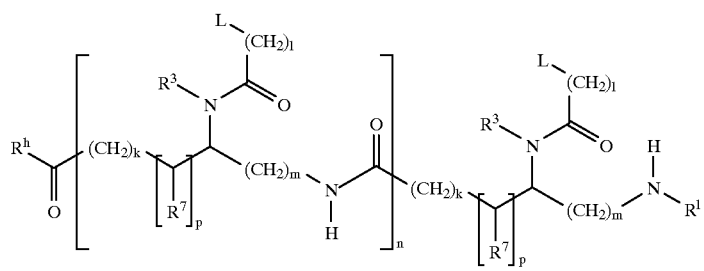

Formula V wherein:
each L is independently selected from the group consisting of hydrogen, phenyl, heterocyclic moieties, naturally occurring nucleobases, and non-naturally occurring nucleobases;

each $R^7$ is independently selected from the group consisting of hydrogen and the side chains of naturally occurring alpha amino acids;

n is an integer greater than 1, each k, l, and m is, independently, zero or an integer from 1 to 5;

each p is zero or 1;

$R^h$ is OH, NH₂ or —NHLysNH₂; and $R^i$ is H or —COCH₃.

Techniques for the synthesis of preferred nucleic acid analogues are to be found in WO-A-92/20703.

EXAMPLE 1

The PNA $T_{10}$-LysNH$_2$ was synthesised as in Egholm, M., Buchardt, O., Nielsen, P. E. and Berg, R. H. (1992) "J. Amer. Chem. Soc." 114, 1895–1897 and Egholm, M., Buchardt O., Nielsen, P. E. and Berg, R. H. (1992) "J. Amer. Chem. Soc." 114, 9677–9678. The plasmid pT10KS was constructed by cloning the complementary oligonucleotides 5'-GATCCT$_{10}$G and 5'-GATCCA$_{10}$G into respective strands at the BamHI site of the Bluescript KS+plasmid (Stratagene). The control plasmid pCKS was constructed by cloning a 99bp PCR fragment (with no target sites for the PNA used in this example) into the SmaI site of the bluescript KS+plasmid. Using standard techniques plasmids were isolated from selected clones of recombinant *E. Coli* JM103, purified by buoyant density centrifugation in CsCl gradients and sequenced by the dideoxy method.

The following oligonucleotide primers were used in the PCR reactions: reverse primer (5'-CACACAGGAAACAGCTATGAC-SEQ ID NO:1 and forward primer (5'-GTAAAACGACGGCCAGT-SEQ ID NO:2). PCR amplifications were carried out in a 50 μl volume containing 1 ng of each plasmid, 0.2 μM of each primer, 200 μM dNTP, 10 mM Tris-HCl, pH 8,3 (at 25° C.), 10 mM KCl, and 3 mM MgCl$_2$.

The concentrations of the PNA employed were 0 μM, 13.2 μM, 6.6 μM, 3.2 μM, 1.6 μM, 0.8 μM, 0.4 μM and 0.2 μM.

The PCR reactions were overlain with 2 drops of paraffin oil and incubated at 90° C. for 2 minutes before the amplification process was initiated by the addition of 3U of Stoffel polymerase (Perkin Elmer Cetus). A LEP amplifier machine (IgG Biotech) was used in all experiments and standard PCR cycle profiles were 96° C., 2 min –55° C., 3 min –35° C., 1 min –65° C., 2 min –35 cycles.

To ensure that the formation of the PNA/DNA complexes preceded PCR primer binding and extension the normal 3 step PCR cycle was expanded with a distinct PNA annealing step at 55° C. a temperature well above the $T_m$ of the PCR primers.

Products resulting from the PCR process were separated by gel electrophoresis and stained using ethidium bromide using standard techniques. A Polaroid™ photograph was taken of the stained gel and the intensity of the bands was assessed by visual inspection.

Table 1 shows the result of PCR inhibition in the presence of increasing amounts of PNA $T_{10}$-LysNH$_2$. The two plasmid templates described above were used; namely the pT10KS plasmid which directs the amplification of a 246 bp fragment containing an A$_{10}$ target site and the control plasmid, pCKS, which directs the amplification of a 329 bp non-target fragment.

The ability to clamp the PCR reaction is indicated using the following nomenclature: ++=PCR product; +=some PCR product and –=no PCR product; NT =not tested.

TABLE 1

| Plasmid | Concentrations of PNA (μm) | | | | | | | |
|---|---|---|---|---|---|---|---|---|
| | 0 | 0.2 | 0.4 | 0.8 | 1.6 | 3.2 | 6.6 | 13.2 |
| p T10KS | ++ | ++ | ++ | ++ | + | – | – | – |
| pCKS | NT | NT | NT | NT | NT | NT | NT | ++ |

When the PNA $T_{10}$-LysNH$_2$ is either absent or present in a concentration equal to or below 1.6 μM the pT10KS plasmid directs the synthesis of the expected 246 bp PCR fragment. At concentration at or about 3.2 μM PNA $T_{10}$-LysNH$_2$, however, no product is produced. The absence of product is not due to a non-specific inhibitory effect of PNA $T_{10}$-LysNH$_2$ on the PCR reaction, since even at the highest concentration used (13.2 μM), PNA $T_{10}$-LysNH$_2$ will not inhibit the amplification of the expected 329 bp fragment from the pCKS control plasmid. This, it is seen that the PNA $T_{10}$-LysNH$_2$ can prevent the amplification of its cognate target DNA in a sequence specific manner. The concentration dependence of inhibition is quite steep.

Virtually no inhibition is observed at 0.8 μM PNA while more than 75% inhibition takes place at 1.6 μM and total inhibition is seen at 3.2 μM PNA.

Taking a sample containing an unknown quantity of the pT10KS plasmid, one may repeat the above procedure seeking to find a dilution of the sample plasmid at which the profile of inhibition using the concentrations of PNA used above matches the results shown in FIG. 1, so establishing the concentration of plasmid.

More preferably however, one may simply calculate the quantity of template by finding the critical quantity of PNA in μM required to inhibit amplification and relying on proportionality between this and the amount of template DNA in ng by a factor of 1 ng/3.2 μM derived from the results above.

EXAMPLE 2

Plasmid and primers used in this example are as follows:
Plasmid p62-1

The plasmid was constructed in two steps. First the complementary oligonucleotides (5'-GATCCTGTACGTCACAACTA-3'-SEQ ID NO:3 and 5'-BATCTAGTTGTGCGTACAG-3'SEQ ID NO:4) comprising the recognition sequence for PNA62 (H-TGTACGTCACAACTA-Gly-NH2(SEQ ID NO:7)) were cloned into the BamHI site of the plasmid pUC19 to yield p62. Second, a 556 bp PstI/HindIII fragment of *E. coli* phase λ genome was cloned into the PstI/HindIII site of p62 to yield p62-1.
Primers Two primers were synthesised with the following sequence: reverse primer 5'-GAAACAGCTATGAC-3'-SEQ ID NO:5 and forward primer 5'-TGTACGTCACAACTA-3'-SEQ ID NO:6 (the sequence of the forward primer is identical to the sequence of the PNA62). In a PCR reaction the forward and reverse primer together with the p62-1 plasmid direct the amplification of a 659 bp fragment.

PCR reactions were set-up containing either 1 ng, 5 ng or 25 ng of plasmid p62-1, reverse and forward PCR primers and various concentrations of PNA 62. Each PCR reaction (50 μl) contained 200 μM dNTP, 10 mM Tris-HCl pH 9.9 (20° C.), 50 μM KCl, 1.5 mM MgCl$_2$, 0.01% gelatine, 0.1% Triton X-100, 1U supertaq enzyme (Stratagene), 10 pmol of each of the two PCR primers and PNAs and p 62-1 plasmid as indicated below in Table 2. PCR conditions were 96° C. 2 min, 65° C. 2 min, 35° C. 30 sec, 70° C. 2 min–30 cycles. The ability to clamp the PCR reaction is indicated using the following nomenclature: ++=PCR product; +=some PCR product and –=no PCR product.

TABLE 2

| | PNA Concentration | | | | | |
|---|---|---|---|---|---|---|
| | None | 1.63 μM | 325 nM | 65 nM | 13 nM | 2.6 nM |
| 1 ng plasmid | ++ | – | – | – | ++ | ++ |
| 5 ng plasmid | ++ | – | – | + | ++ | ++ |
| 25 ng plasmid | ++ | – | + | ++ | ++ | ++ |

When 1 ng of plasmid was used the concentration of PNA that effectively clamped the PCR reaction was found to be 65nM. When the amount of plasmid target was increased five fold (from 1 to 5 ng) the PNA concentration that was required for efficient clamping was proportionally increased to 325 nM. Similarly, increasing the initial plasmid target 25 fold required a 25 fold increase in PNA (1.63 μM) for efficient clamping to take place. Thus, the QI or PCR clamp method can be used to quantitate the initial amount of target in the reaction.

Had the quantitative plasmid content of the sample containing 5 ng been unknown, it could readily have been deduced from the results obtained at 1 ng of plasmid, used as a calibration curve, and the cut-off figure of 65 nM found for effective clamping of the amplification of the unknown (5 ng plasmid) sample.

It should be noted that, in Example 1 and Example 2, only one nucleic acid analogue is employed and this is directed against one PCR primer site only. Hence a linear amplification process driven by the non-inhibited primer will take place in these experiments. Such linearly amplified material will not be detected by the gel electrophoetic method described here because of sensitivity limitations. To achieve total inhibition of a PCR process it is necessary to employ two nucleic acid molecules directed at either both primers or at both strands of the double stranded nucleic acid target. This will be important if more senistive methods of detection than gel electrophoresis/staining by ethidium bromide are to be employed.

Whilst the invention has been described with reference to the preferred embodiments illustrated by the Examples above, many variations and modifications are possible within the scope of the invention.

Also, the invention includes a kit for use in quantifying an amount of target nucleic acid in a sample, comprising reagents for use in an amplification procedure to amplify a sequence in said nucleic acid, and at least two non-complementary nucleic acid analogue sequences each for hybridising to a sequence to be amplified respectively in a strand of said target nucleic acid and a nucleic acid strand complementary thereto to prevent amplification thereof.

The nucleic acid sequences referred to above are detailed in the following listing.

We claim:

1. A quantitative assay procedure for determining a nucleic acid comprising the following steps:
    amplifying a nucleic acid template in the presence of a nucleic acid analogue which inhibits amplification by selective interaction with said nucleic acid template, wherein either the amount of said nucleic acid template or the amount of said nucleic acid analogue is known or later determined,
    determining the presence, absence or amount of any amplification product produced as a measure of the success, failure, or degree of success of said amplification, and
    determining the amount of said nucleic acid template based on the amount of nucleic acid analogue required to inhibit amplification or determining the amount of said nucleic acid analogue based on the amount of nucleic acid template inhibited by said nucleic acid analogue.

2. The assay procedure according to claim 1, wherein said nucleic acid template is present in an unknown quantity.

3. The assay procedure according to claim 1, further comprising repeating said assay procedure one or more times using at least two different amounts of said nucleic acid analogue in order to determine the amount of said nucleic acid analogue needed to inhibit said amplification procedure.

4. The assay procedure according to claim 1, further comprising the addition of a primer which binds to the same part of the nucleic acid template as said nucleic acid analogue.

5. The assay procedure according to claim 1, wherein the nucleic acid analogue comprises a polymeric strand which includes a sequence of ligands bound to a backbone selected from the group consisting of linked polyamide, polythioamide, polysuiphinamide and polysulphonamide moieties, wherein said analogue hybridizes to a template nucleic acid.

6. The assay procedure according to claim 1, wherein said nucleic acid analogue hybridizes to a template nucleic acid to form a hybrid which is more stable against denaturation by heat than a hybrid between a conventional deoxyribonucleotide corresponding in sequence to said analogue and said template nucleic acid.

7. The assay procedure according to claim 5, wherein said nucleic acid analogue is a peptide nucleic acid in which said backbone is a polyamide backbone, wherein each ligand is bonded directly or indirectly to an aza nitrogen atom in said backbone, and said ligand bearing nitrogen atoms are separated from one another in said backbone by from 4 to 8 intervening atoms.

8. The assay procedure according to claim 1, wherein the nucleic acid analogue hybridizes to a double-stranded nucleic acid template in which one strand has a sequence complementary to said analogue and the other strand has a sequence which is not complementary to said analogue, in such a way as to displace the other strand from the strand which is complementary to said analogue.

9. A kit for quantifying a target nucleic acid in a sample, comprising (a) at least two nucleic acid analogue sequences including a first and a second nucleic acid analogue sequence which are non complementary to each other, the first analogue hybridizing to a sequence to be amplified in a strand of said target nucleic acid and the second analogue hybridizing to a nucleic acid strand complementary thereto, and wherein said nucleic acid analogue sequences prevent amplification of said target nucleic acid, and (b) amplification buffers and reagents.

10. The kit according to claim 9, further comprising at least two amplification primers wherein said nucleic acid analogue sequences compete with said primers to hybridize to said target nucleic acid.

11. The kit according to claim 9, further comprising at least two amplification primers, wherein said nucleic acid analogue sequences hybridize to said target nucleic acid between the binding sites for said primers.

12. The procedure according to claim 1, further comprising the addition of a second nucleic acid analogue which inhibits amplification by selective interaction with said nucleic acid template, wherein said nucleic acid analogue and said second nucleic acid analogue hybridize to different sites on said nucleic acid template.

13. The assay procedure according to claim 1, wherein the nucleic acid analogue has the formula 1:

Formula 1

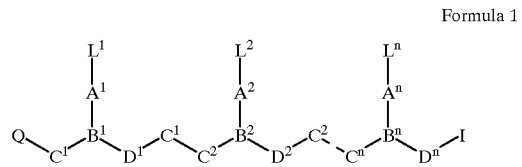

wherein:

n is at least 2, each of $L^1$–$L^n$ is independently selected from the group consisting of hydrogen, hydroxy, ($C_1$–$C_4$) alkanoyl, naturally occurring nucleobases, non-naturally occurring nucleobases, aromatic moieties, DNA intercalators, nucleobase-binding groups, heterocyclic moieties, and reporter ligands, wherein at least one of L1–Ln is a nucleobase binding group;

each of $C^1$–$C^n$ is $(CR^6R^7)_y$ where $R^6$ is hydrogen and $R^7$ is selected from the group consisting of the side chains of naturally occurring alpha amino acids, or $R^6$ and $R^7$ are independently selected from the group consisting of hydrogen, ($C_2$–$C_6$) alkyl, aryl, aralkyl, heteroaryl, hydroxy, ($C_1$–$C_6$) alkoxy, ($C_1$–$C_6$) alkylthio, $NR^3R^4$ and $SR^5$, where $R^3$ and $R^4$ are as defined below, and $R^5$ is selected from the group consisting of hydrogen, ($C_1$–$C_6$) alkyl, hydroxy, alkoxy, and alkylthio-substituted ($C_1$–$C_6$) alkyl or $R^6$ and $R^7$ taken together complete an alicyclic or heterocyclic system each of $D^1$–$D^n$ is $(CR^6R^7)_z$ where $R^6$ and $R^7$ are as defined above;

each of y and z is zero or an integer from 1 to 10, the sum y+z is from 2 to 10;

each of $G^1$–$G^{n-1}$ is $-NR^3CO-$, $-NR^3CS-$, $-NR^3SO-$ or $-NR^3SO_2-$, in either orientation, wherein $R^3$ is as defined below;

each of $A^1$–$A^n$ and $B^1$–$B^n$ are selected such that:
(a) A is a group of formula (IIa), (IIb), (IIc) or (IId), and B is N or $R^3$N+; or
(b) A is a group of formula (IId) and B is CH;

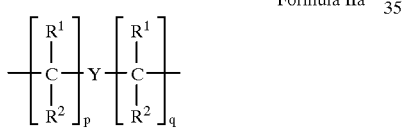

Formula IIa

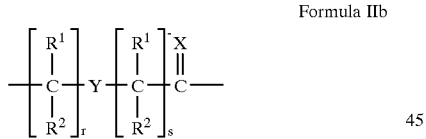

Formula IIb

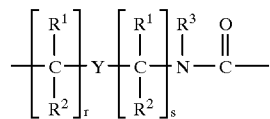

Formula IIc

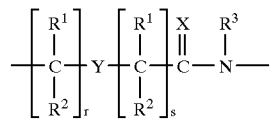

Formula IId wherein:

X is O, S, Se, $NR^3$, $CH_2$ or $C(CH_3)_2$;

Y is a single bond, O, S or $NR^4$;

each of p and q is zero or an integer from 1 to 5, the sum p+q is not more than 10;

each of r and s is zero or an integer from 1 to 5, the sum r+s is not more than 10;

each of $R^1$ and $R^2$ is independently selected from the group consisting of hydrogen, ($C_1$–$C_4$) alkyl which may be hydroxy- or alkoxy- or alkylthio-substituted, hydroxy, alkoxy, alkylthio, amino and halogen; and each $R^3$ and $R^4$ is independently selected from the group consisting of hydrogen, ($C_1$–$C_4$) alkyl, hydroxy-substituted ($C_1$–$C_4$) alkyl, alkoxy-substituted ($C_1$–$C_4$) alkyl, alkylthio-substituted ($C_1$–$C_4$) alkyl, hydroxy, alkoxy, alkylthio and amino;

Q is $-CO_2H$, $-CONR'R''$, $-SO_3H$ or $-SO_2NR'R''$ or an activated derivative of $-CO_2H$ or $-SO_3H$; and I is $-NR'R''$, where R' and R'' are independently selected from the group consisting of hydrogen, alkyl, amino protecting groups, reporter ligands, intercalators, chelators, peptides, proteins, carbohydrates, lipids, steroids, nucleosides, nucleotides, nucleotide diphosphates, nucleotide triphosphates, oligoribonucleotides and oligodeoxyribonucleotides, oligonucleosides and soluble and non-soluble polymers.

14. The assay procedure according to claim 13, wherein said nucleic acid analogue is selected from the group consisting of the formulas III, IV and V;

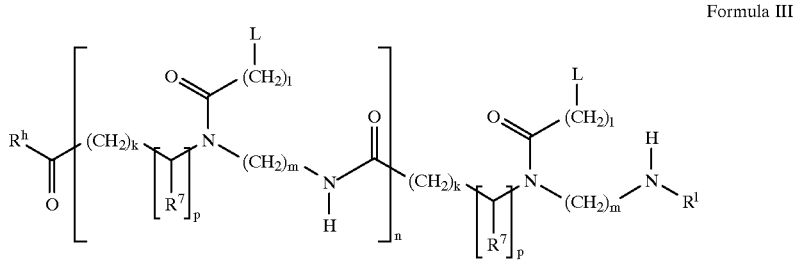

Formula III

Formula IV

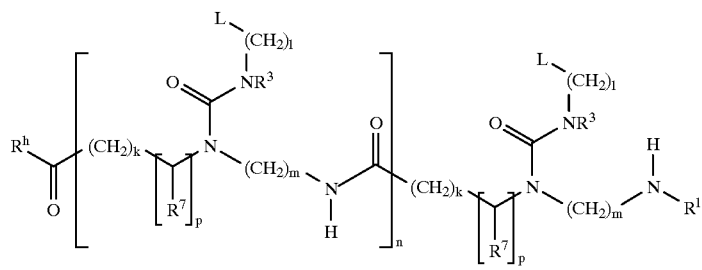

Formula V

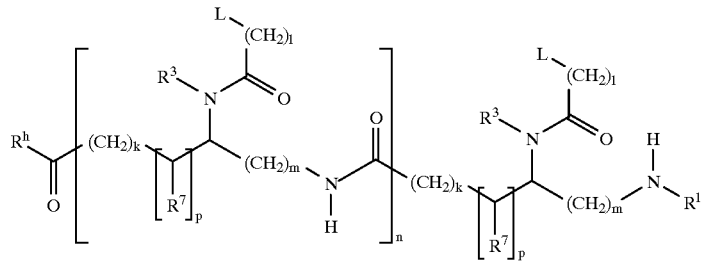

wherein:
- L is selected from the group consisting of hydrogen, phenyl, heterocyclic moieties, naturally occurring nucleobases, and non-naturally occuring nucleobases;
- each $R^7$ is independently selected from the group consisting of hydrogen and the side chains of naturally occurring alpha amino acids;
- n is an integer greater than 1,
- k and l are independently, zero or an integer from 1 to 5;
- m is an integer from 1 to 5;
- p is zero or 1;
- $R^h$ is OH, $NH_2$ or —$NHLysNH_2$; and
- $R^1$ is H or $COCH_3$, wherein when k is zero, p is 1.

* * * * *